US005725731A

United States Patent [19]

Brungardt et al.

[11] Patent Number: 5,725,731

[45] Date of Patent: Mar. 10, 1998

[54] 2-OXETANONE SIZING AGENTS COMPRISING SATURATED AND UNSATURATED TAILS, PAPER MADE WITH THE 2-OXETANONE SIZING AGENTS, AND USE OF THE PAPER IN HIGH SPEED CONVERTING AND REPROGRAPHIC OPERATIONS

[75] Inventors: Clement L. Brungardt, Oxford, Pa.; John C. Gast, Hockessin; Jian-Jian Zhang, Wilmington, both of Del.

[73] Assignee: Hercules Incorporated, Wilmington, Del.

[21] Appl. No.: 439,057

[22] Filed: May 8, 1995

[51] Int. Cl.[6] .......... D21C 3/20; C07D 305/12

[52] U.S. Cl. .......... 162/72; 162/75; 162/158; 162/173; 162/179; 549/263; 549/328; 549/329; 549/510

[58] Field of Search .......... 428/537.5, 378, 428/268, 389, 394, 406; 252/8, 9, 52 A, 54, 54.6, 56 R, 58; 106/243, 244; 524/300, 487; 549/263, 328, 329, 510; 162/158, 173, 179, 72, 75

[56] References Cited

U.S. PATENT DOCUMENTS

| | | | |
|---|---|---|---|
| 2,383,863 | 8/1945 | Hueter | 260/550 |
| 2,772,969 | 12/1956 | Reynolds, Jr. et al. | 162/179 |
| 2,776,226 | 1/1957 | Hart | 117/64 |
| 2,785,067 | 3/1957 | Osberg | 92/21 |
| 2,959,512 | 11/1960 | Roberson | 154/38 |
| 2,992,964 | 7/1961 | Werner et al. | 162/178 |
| 3,251,732 | 5/1966 | Aldrich | 162/179 |
| 3,311,532 | 3/1967 | Kulick et al. | 162/179 |
| 3,392,085 | 7/1968 | Oliver | 162/175 |
| 3,404,064 | 10/1968 | Feazel | 162/179 |
| 3,992,345 | 11/1976 | Dumas | 524/612 |
| 4,240,935 | 12/1980 | Dumas | 524/72 |
| 4,295,931 | 10/1981 | Dumas | 162/158 |
| 4,317,756 | 3/1982 | Dumas | 524/607 |
| 4,382,129 | 5/1983 | Banker | 524/598 |
| 4,522,686 | 6/1985 | Dumas | 162/158 |
| 4,687,519 | 8/1987 | Trzasko et al. | 106/211 |
| 4,698,259 | 10/1987 | Hervey | 428/378 |
| 4,859,244 | 8/1989 | Floyd | 106/243 |
| 4,861,376 | 8/1989 | Edwards et al. | 106/123 |
| 4,919,724 | 4/1990 | Cenisio et al. | 106/199 |
| 4,927,496 | 5/1990 | Walkden | 162/136 |
| 5,026,457 | 6/1991 | Eichinger et al. | 162/158 |
| 5,032,320 | 7/1991 | Gutierrez et al. | 252/565 |
| 5,484,952 | 1/1996 | Nolan et al. . | |

FOREIGN PATENT DOCUMENTS

| | | |
|---|---|---|
| 0 624 579 | 11/1994 | European Pat. Off. . |
| 629741 | 12/1994 | European Pat. Off. . |
| 666368 | 8/1995 | European Pat. Off. . |
| 4-36258 | 2/1992 | Japan . |
| 4-36259 | 2/1992 | Japan . |
| 427940 | 5/1983 | Sweden . |

OTHER PUBLICATIONS

Pamak® "Fatty Acids Distilled Tall Oils Tall Oil Light Ends Typical Properties and Uses" (Hercules) (1989).

Pamolyn® Fatty Acids (Hercules) (1989).

"High Purity, Low-Rosin Tall Oil Fatty Acids" (Description of Pamak 1, 2 and 4A) (Jun. 29, 1994).

Technical Bulletin 145S, Specifications and Characteristics of Emery Oleochemicals (Henkel Corporation, Emery Group)(May 1993).

Union Camp Oleochemicals® Product Data, Unidyme® 14 Distilled Dimer Acids (Aug. 1995).

Union Camp Oleochemicals® Product Data, Unidyme® 18 Dimer Acids (Aug. 1995).

Emerox® 1110 Azelaic Acid (Henkel Corporation)(Mar. 1996).

Emerox® 1144 Azelaic Acid (Henkel Corporation)(Mar. 1996).

Derwent Abstract of JP 2068399, published Mar. 7, 1990 (Arakawa Kagaku Kogyo)(Previously improperly listed as Derwent Abstract of JP 90-119139).

Derwent Abstract of JP 1168992, published Jul. 4, 1989 (Nippon Oils & Fats KK) (Previously improperly listed as Derwent Abstract of JP 89-232552).

C.L. Brungardt & J.C. Gast, "Alkenyl-Substituted Sizing Agents for Precision Converting Grades of Fine Paper", Tappi Papermakers' Conference Proceedings (1996).

J. Borch, "Neutral/Alkaline Paper Making", Tappi Neutral/Alkaline Papermaking Short Course, Notes: 39 (1990).

J. Borch & R. G. Zvendesn, "Paper Material Considerations for System Printers", IBM Journal, R&D 28, No. 3, pp. 285-291 (1984).

M.A. Meixner, "Alkaline Fine Paper Sizing Technology — Recent Developments" (1995).

"Hercules Develops Alkaline PaperSize Designed For Precision Converting Grades" (Jan. 17, 1994).

Brungardt,C.L. & Gast,J.C., "Improving the Converting and End-Use Performance of Alkaline Fine Paper", Tappi Paper Makers Conf. Proceedings, Apr. 1994.

Meixner,M.A. & Ramaswamy,S., "A Converting and End-Use Approach to Alkaline Fine Paper Size Development",Tappi Paper Makers Conf. Proceedings, Apr. 1994.

Gast, J.C., "Improving the Performance of Alkaline Fine Paper On The IBM 3800(R) Laser Printer", Tappi Paper Makers Conf. Proceedings, 1991, p. 1.

(List continued on next page.)

*Primary Examiner*—H. Thi Le
*Attorney, Agent, or Firm*—Mark D. Kuller

[57] ABSTRACT

A sizing composition for fine paper that does not encounter machine feed problems in high-speed converting or reprographic operations is not solid at 35° C. and comprises a mixture of 2-oxetanone compounds that are the reaction product of a reaction mixture comprising (a) a feedstock comprising primarily unsaturated fatty acids and (b) a feedstock comprising primarily saturated fatty acids, or acid halides thereof, provided that at least 20 mole % of the reaction mixture fatty acids comprise saturated fatty acids and at least 20 mole % of the reaction mixture fatty acids comprise unsaturated fatty acids.

49 Claims, No Drawings

OTHER PUBLICATIONS

Abstracts from Chemical Patents Index, Derwent Publications, Week 9304, Mar. 17, 1993.

Farley,C.E. & Wasser,R.B., "The Sizing of Paper (Sec. Ed.)", Sizing With Alkenyl Succinic Anhydride, 1989, p. 51.

IBM 3825 Page Printer Paper Reference (G544–3483), Sep. 1988.

Walkden,S.A., "Sizing With AKD — A Review of Trends, Theories and Practical In–Mill Application and Troubleshotting", Tappi Neutral/Alkaline Papermaking Short Course (Orlando, FL), pp. 67–70, Oct. 16–18, 1990.

W.O. Kincannon, Jr.et al, "D. Sizing With Alkylketene Dimers", *Internal Sizing of Paper and Paperboard, pp. 157–170* (J.W. Swanson, Ed., Tappi, 1971).

Aquapel® Sizing Agent Trade Literature (© Hercules Powder Company, 1963).

Dumas and Evans, "AKD–Cellulose Reactivity in Papermaking Systems", *1986 Papermakers Conference* (Tappi Press, 1986).

Bottorff, "The AKD Sizing Mechanism: A More Definitive Description" (Tappi Press, 1993).

Bottorff, "The AKD Sizing Mechanism: A More Definitive Description", Tappi Journal, vol. 77, No, 4, Apr. 1994).

Hercules Powder Company, Paper Makers Chemical Department, "Properties and Uses of Aquapel®" (1960).

2-OXETANONE SIZING AGENTS COMPRISING SATURATED AND UNSATURATED TAILS, PAPER MADE WITH THE 2-OXETANONE SIZING AGENTS, AND USE OF THE PAPER IN HIGH SPEED CONVERTING AND REPROGRAPHIC OPERATIONS

FIELD OF THE INVENTION

This invention relates to sizing compositions for paper made under alkaline conditions, paper sized with the sizing compositions, and processes for using the paper.

BACKGROUND OF THE INVENTION

The amount of fine paper produced under alkaline conditions has been increasing rapidly, encouraged by cost savings, the ability to use precipitated calcium carbonate, an increased demand for improved paper permanence and brightness, and an increased tendency to close the wet end of the paper machine.

Current applications for fine paper, such as high-speed photocopies, envelopes, forms bond including computer printer paper, and adding machine paper require particular attention to sizing before conversion or end use. The most common sizing agents for fine paper made under alkaline conditions are alkenyl succinic anhydride (ASA) and alkyl ketene dimer (AKD). Both types of sizing agents have a reactive functional group that covalently bonds to cellulose fiber and hydrophobic tails that are oriented away from the fiber. The nature and orientation of these hydrophobic tails cause the fiber to repel water.

Commercial AKD's, containing one β-lactone ring, are prepared by the dimerization of the alkyl ketenes made from two saturated, straight-chain fatty acid chlorides; the most widely used being prepared from palmitic and/or stearic acid. Other ketene dimers, such as the alkenyl based ketene dimer (Aquapel® 421, available from Hercules Incorporated, Wilmington, Del., U.S.A.), have also been used commercially. Ketene multimers, containing more than one β-lactone ring, have been described in Japanese Kokai 168992/89, the disclosure of which is incorporated by reference in its entirety.

Although AKD sizing agents are commercially successful, they have disadvantages. This type of sizing agent has been associated with handling problems in the typical high-speed conversion operations required for the current uses of fine paper made under alkaline conditions (referred to as alkaline fine paper). The problems include reduced operating speed in forms presses and other converting machines, double feeds or jams in high-speed copiers, and paper welding and registration errors on printing and envelope-folding equipment that operate at high speeds.

These problems are not normally associated with fine paper produced under acid conditions (acid fine paper). The types of filler and filler addition levels used to make alkaline fine paper differ significantly from those used to make acid fine paper, and can cause differences in paper properties such as stiffness and coefficient of friction, which affect paper handling. Alum addition levels in alkaline fine paper, which contribute to sheet conductivity and dissipation of static, also differ significantly from those used in acid fine paper. This is important because the electrical properties of paper affect its handling performance. Sodium chloride is often added to the surface of alkaline fine paper to improve its performance in end use.

The typical problems encountered with the conversion and end use handling of alkaline fine paper involve:

1. Paper properties related to composition of the furnish;
2. Paper properties developed during paper formation; and
3. Problems related to sizing.

The paper properties affected by papermaking under alkaline conditions that can affect converting and end-use performance include:

Curl
Variation in coefficient of friction
Moisture content
Moisture profile
Stiffness
Dimensional stability
MD/CD strength ratios One such problem has been identified and measured as described in "Improving the Performance of Alkaline Fine Paper on the IBM 3800 Laser Printer," TAPPI Paper Makers Conference Proceedings (1991), the disclosure of which is incorporated by reference in its entirety. The problem occurs when using an IBM 3800 high-speed continuous forms laser printer that does not have special modifications intended to facilitate handling of alkaline fine paper. That commercially significant laser printer therefore can serve as an effective testing device for defining the convertibility of various types of sized paper on state-of-the-art converting equipment and its subsequent end use performance. In particular, the phenomenon of "billowing" gives a measurable indication of the extent of slippage on the IBM 3800 printer between the undriven roll beyond the fuser and the driven roll above the stacker.

Such billowing involves a divergence of the paper path from the straight line between the rolls, which is two inches above the base plate, causing registration errors and dropped folds in the stacker. The rate of billowing during steady-state running time is measured as the billowing height in inches above the straight paper path after 600 seconds of running time and multiplied by 10,000.

Typical alkaline AKD-sized fine paper using a size furnish of 2.2 lbs. per ton (1 kg per 0.9 metric ton) of paper shows an unacceptable rate of billowing, typically on the order of 20 to 80. Paper handling rates on other high-speed converting machinery, such as a Hamilton-Stevens continuous forms press or a Winkler & Dunnebier CH envelope folder, also provide numerical measures of convertibility.

U.S. Ser. No. 08/192,570, filed Feb. 7, 1994, discloses paper sizing agents comprising 2-oxetanone dimers and multimers that are not solid at 35° C. Preferred sizing agents contain unsaturation or chain branching in the pendant hydrocarbon chains. U.S. Ser. No. 08/254,813, filed Jun. 6, 1994, the disclosure of which is incorporated by reference in its entirety, discloses 2-oxetanone sizing agents comprising a mixture of dimers and multimers, where at least 50% of the compounds in the mixture are multimers. Both applications claim improved performance in high-speed converting and reprographic machines compared to sizing obtained with standard alkyl ketene dimer.

However, there is still a need for alkaline fine paper that provides improved handling performance in typical converting and reprographic operations. At the same time, the levels of sizing development need to be comparable to that obtained with the current furnish levels of AKD for alkaline fine paper.

SUMMARY OF THE INVENTION

The sizing composition of this invention for paper made under alkaline conditions is not solid at 35° C. and comprises a mixture of 2-oxetanone compounds that are the reaction product of a reaction mixture comprising (a) a feedstock comprising primarily unsaturated fatty acid and (b) a feedstock comprising primarily saturated fatty acid, provided that about 10–85 mole % of the fatty acid comprises saturated fatty acid and about 90–15 mole % of the fatty acid comprises unsaturated fatty acids. In one preferred embodiment, the 2-oxetanone compounds are 2-oxetanone dimers. In another preferred embodiment, component (c), an alkyl dicarboxylic acid, is present in the reaction mixture. If (c) is present, the 2-oxetanone compounds are a mixture of dimers and multimers.

Preferably the fatty acid comprises about 20–60 mole % saturated fatty acid and about 80–40 mole % unsaturated fatty acid, more preferably about 30–55 mole % saturated fatty acid and about 70–45 mole % unsaturated fatty acid.

Preferably the 2-oxetanone sizing composition is not solid at 25° C., more preferably not solid at 20° C. Preferably the composition is liquid at 35° C., more preferably liquid at 25° C., and most preferably liquid at 20° C.

Preferably the fatty acid is monocarboxylic acid or monocarboxylic acid halide having 6–26 carbon atoms, more preferably 12–22 carbon atoms, and most preferably 16–18 carbon atoms.

Preferably the saturated fatty acid is selected from the group consisting of stearic, isostearic, myristic, palmitic, margaric, pentadecanoic, decanoic (capric), undecanoic, dodecanoic (lauric), tridecanoic, nonadecanoic, arachidic, and behenic acids and acid chlorides, and mixtures thereof. Preferably the unsaturated fatty acid is selected from the group consisting of oleic, linoleic, dodecenoic, tetradecenoic (myristoleic), hexadecenoic (palmitoleic), octadecadienoic (linolelaidic), octadecatrienoic (linolenic), eicosenoic (gadoleic), eicosatetraenoic (arachidonic), docosenoic (erucic), docosenoic (brassidic), and docosapentaenoic (clupanodonic) acids and acid chlorides, and mixtures thereof.

Preferably the saturated fatty acid feedstock comprises at least 80 mole % saturated fatty acid and the unsaturated fatty acid feedstock comprises at least 70 mole % unsaturated fatty acid, more preferably at least about 95 mole % saturated fatty acid and at least about 90 mole % unsaturated fatty acid respectively.

Preferably the mole ratio of the unsaturated fatty acid feedstock to the saturated fatty acid feedstock is about 1:1–4:1, preferably about 1:1, about 1:4 or about 7:3.

Preferably, according to one embodiment, the product is a 2-oxetanone dimer. Preferably, according to another embodiment, the reaction mixture additionally comprises (c) an alkyl dicarboxylic acid having 6–44 carbon atoms. Preferably the dicarboxylic acid has 8–36 carbon atoms, more preferably 9–10 carbon atoms.

In addition, this invention is directed to a sizing composition that is not a solid at 35° C. and comprises a mixture of 2-oxetanone compounds that are the reaction mixture comprising fatty acid comprising about 10–85 mole % saturated fatty acid and 90–15 mole % unsaturated fatty acid. Preferably, the fatty acid comprises about 20–60 mole saturated fatty acid and about 80–40 mole % unsaturated fatty acid. More preferably the fatty acid comprises about 30–55 mole % saturated fatty acid and about 70–45 mole % unsaturated fatty acid. Preferably the fatty acid is monocarboxylic acid or monocarboxylic acid halide having 6–26 carbon atoms, more preferably 12–22 carbon atoms, and most preferably 16–18 carbon atoms. In one preferred embodiment, the product is a 2-oxetanone dimer. In another preferred embodiment, the fatty acid is reacted with at least one dicarboxylic acid having 8–44 carbon atoms.

The invention is also directed to paper made under alkaline conditions and sized with the aforementioned sizing composition. According to one preferred embodiment, the paper also comprises a water-soluble inorganic salt of an alkali metal, preferably NaCl. The invention is also directed to using the paper in high speed converting or reprographic operations.

The invention is further directed to a process of preparing a 2-oxetanone sizing agent comprising (i) providing (a) at least one feedstock comprising primarily saturated fatty acid, and (b) at least one second feedstock comprising primarily saturated fatty acid, and (ii) reacting them to form a 2-oxetanone sizing agent that is not a solid, provided that about 10–85 mole % of the fatty acid comprises saturated fatty acid and about 90–15 mole % of the fatty acid comprises unsaturated fatty acid. In one preferred embodiment, the product is a 2-oxetanone dimer. In another preferred embodiment, (c) at least one dicarboxylic acid having 8–44 carbon atoms is also reacted.

According to another embodiment, the invention is directed to a process for preparing a 2-oxetanone sizing agent comprising providing unsaturated and saturated fatty acids, the fatty acids comprising about 10–85 mole % of saturated fatty acid and about 90–15 mole % unsaturated fatty acid, and reacting them to form a 2-oxetanone sizing agent that is not a solid at 35° C. In one preferred embodiment, the product is 2-oxetanone dimer. In another preferred embodiment, component (c) is at least one dicarboxylic acid having 8–44 carbon atoms is also reacted.

The invention is also directed to an aqueous emulsion comprising water and 1–60 weight %, preferably 6–50 weight % and more preferably 10–30 weight %, of the sizing composition.

The paper according to the invention is capable of performing without encountering significant machine-feed problems in high speed converting and reprographic operations. Machine-feed problems on high-speed converting machines or during reprographic operations are defined as significant in any specific conversion or reprographic application if they cause misfeeds, poor registration, or jams to a commercially unacceptable degree as will be discussed below, or cause machine speed to be significantly reduced.

DETAILED DESCRIPTION OF THE INVENTION

Herein, "fatty acid" is frequently used to mean a fatty acid or fatty acid halide for convenience. The person of ordinary skill in the art will recognize that this is used herein when referring to fatty acids for use in making sizing compositions since fatty acids are converted to acid halides in the first step of making 2-oxetanone compounds, and that the invention may be practiced by stating with fatty acids or fatty acids already converted to their halide. Further, the person or ordinary skill in the art will readily recognize that "fatty acid" generally refers to a blend or mixture of fatty acids or fatty acid halides since fatty acids are generally derived from natural materials and thus normally are blends or mixtures.

The alkaline sizing agents of this invention that give levels of sizing comparable to those obtained with current commercial AKD sizing technology and improved handling performance in typical end use and converting operations, have at least one reactive 2-oxetanone group and pendant hydrophobic hydrocarbon groups. The mixture of 2-oxetanone compounds is not a solid at 35° C. (not substantially a crystalline, semicrystalline, or waxy solid, i.e., it flows on heating without heat of fusion). Preferably the mixture of 2-oxetanone compounds is not a solid at 25° C., more preferably even at 20° C. Even more preferably, the sizing agent according to the invention is a liquid at 35° C., more preferably at 25° C. and most preferably at 20° C. The references to "liquid" of course apply to the sizing agent per se and not to an emulsion or other composition.

The mixture of 2-oxetanone compounds is prepared using methods known for the preparation of standard ketene dimers. In the first step, acid chlorides are formed from a mixture of saturated and unsaturated fatty acids, or a mixture of fatty acids and a dicarboxylic acid in the case of multimers, using $PCl_3$ or another chlorinating agent. The acid chlorides are then dimerized in the presence of tertiary amines (including trialkyl amines and cyclic alkyl amines), preferably triethylamine, to form the ketene dimer or multimer. Stable emulsions of these sizing agents can be prepared in the same way as standard AKD emulsions.

The fatty acids used to prepare the 2-oxetanone compounds of this invention are monocarboxylic acids having 10–26 carbon atoms, preferably 14–22 carbon atoms, and most preferably 16–18 carbon atoms. Examples of saturated fatty acids include, for example, stearic, isostearic, myristic, palmitic, margaric, pentadecanoic, decanoic (capric), undecanoic, dodecanoic (lauric), tridecanoic, nonadecanoic, arachidic, and behenic acids. Examples of unsaturated fatty acids include, for example, oleic, linoleic, dodecenoic, tetradecenoic (myristoleic), hexadecenoic (palmitoleic), octadecadienoic (linolelaidic), octadecatrienoic (linolenic), eicosenoic (gadoleic), eicosatetraenoic (arachidonic), docosenoic (erucic), docosenoic (brassidic), and docosapentaenoic (clupanodonic) acids.

One or more saturated or unsaturated fatty acid can be used. The mixture of saturated and unsaturated fatty acids can result from the use of separate feeds, one which comprises primarily saturated and the other which comprises primarily unsaturated fatty acids, or a feed comprising a mixture of saturated and unsaturated fatty acids can be used. Suitable feedstocks comprising primarily unsaturated fatty acids include, for example, Emersol 221 fatty acids, available from Henkel-Emery, Cincinnati, Ohio. Emersol 221 is a mixture of primarily oleic acid and other unsaturated fatty acids and a small amount of saturated fatty acids. Suitable feedstocks comprising primarily saturated fatty acids include, for example, Emery 135 fatty acids, also available from Henkel-Emery. Emery 135 is primarily a mixture of palmitic acid and stearic acid and small amounts of other fatty acids.

If desired, the 2-oxetanone compounds can contain two or more 2-oxetanone rings. These compounds are referred to in this application as "2-oxetanone multimers". These compounds are prepared from acid chlorides of the mixture of saturated and unsaturated fatty acid feedstocks and at least one alkyl dicarboxylic acid as described in Japanese published application 168992/89 and U.S. patent application NOS. 08/192,570, filed Feb. 7, 1994 and 08/254,813, filed Jun. 6, 1994, the disclosures of which are incorporated by reference in their entirety.

The alkyl dicarboxylic acids used to prepare the 2-oxetanone multimers have 8–44 carbon atoms, preferably 9–10, 22 or 36 atoms. Dicarboxylic acids with 9–10 carbon atoms are most preferred. Such dicarboxylic acids include, for example, sebacic, azelaic, 1,10-decanedicarboxylic, suberic, brazylic, and docosanedioic acids. One or more of these dicarboxylic acids can be used.

The 2-oxetanone compounds in the sizing compositions of this invention preferably have the formula:

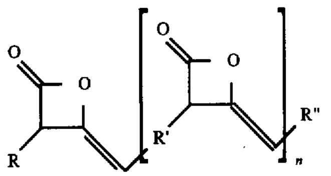

in which n is 0–6, more preferably 0–3, and most preferably 0; R and R" can be the same or different and are selected from the group consisting of straight or branched alkyl or alkenyl groups having at least 4 carbon atoms, preferably 4–24 carbon atoms, more preferably 10–20 carbon atoms, and most preferably 14–16 carbon atoms; and R' is a straight chain alkyl group, preferably a 2–40 carbon straight chain alkyl group, more preferably a 4–32 carbon straight chain alkyl group, and most preferably a 5–8 carbon straight chain alkyl group. When n>0, the compounds are termed 2-oxetanone multimers.

In preparing the 2-oxetanone sizing compositions of this invention, at least 20 mole %, based on the total fatty acid feed, preferably about 20–75%, and most preferably 30–50%, is saturated fatty acids. Preferably, at least 20 mole %, based on the total fatty acid feed, preferably about 80–25%, and most preferably 70–50%, is unsaturated fatty acids.

Preferably the alkaline paper made according to the process of this invention contains a water-soluble inorganic salt of an alkali metal, preferably sodium chloride (NaCl), as well as alum (aluminum sulfate) and precipitated calcium carbonate. However, the paper of this invention will often be made without an alkali metal salt.

The sizing agents of this invention is applied as internal sizing agent that is preferably added to the paper pulp slurry before sheet formation.

The paper of this invention is generally sized at a size addition rate of at least 0.5 lb (0.2 kg), preferably at least about 1.5 lb (0.8 kg), and more preferably at least about 2.2 lb/ton (1 kg/0.9 metric tons) or higher. Typical commercial sizing ranges from ½ lb/ton to 7 lb/ton, preferably from 1 lb/ton to 4 lb/ton and most preferably from 1½ lb/ton to 3 lb/ton. It may be for example, in the form of continuous forms bond paper, perforated continuous forms paper, adding machine paper, envelope-making paper, copy paper, envelope paper or envelopes.

The paper of this invention is capable of performing effectively in tests that measure its convertibility on state-of-the-art converting equipment and its performance on high-speed end use machinery. In particular, the paper according to the invention that can be made into a roll of continuous forms bond paper having a basis weight of about 15 to about 24 lb/1300 $ft^2$ (6.8 to 10.9 kg/121 $m^2$), is capable of running on a high-speed, continuous forms laser printer. When this paper is sized at an addition rate of at least about 1.5 lb/ton (0.68 kg/0.9 metric ton), it is capable of running on the IBM Model 3800 high-speed, continuous forms laser printer without causing a rate of billowing in inches of increase per second×10,000 greater than 5 after ten minutes running time. When the paper is sized at a rate of 2.2 lb/ton (1 kg/0.9 metric ton), the rate of billowing increases per second×10,000 is not greater than 3 after 10 minutes of running time.

Further, the preferred paper according to the invention, that can be made into sheets of 8½×11 inch (21.6 cm×28 cm) reprographic cut paper having a basis weight of about 15 to about 24 lb/1300 $ft^2$ (6.8 to 10.9 kg/121 $m^2$) is capable of running on a high-speed laser printer or copier. When the paper is sized at an addition rate of at least about 1.5 lb/ton (0.68 kg/0.9 metric ton), preferably at least about 2.2 lb/ton (1 kg/0.9 metric ton, it is capable of running on the IBM model 3825 high-speed copier without causing misfeeds or jams at a rate of 5 or less in 10,000, preferably at a rate of 1 or less in 10,000. By comparison, paper sized with standard AKD has a much higher rate of double feeds on the IBM 3825 high speed copier (14 double feeds in 14,250 sheets). In conventional copy machine operation, 10 double feeds in 10,000 is unacceptable. A machine manufacturer considers 1 double feed in 10,000 sheets to be unacceptable.

The paper of this invention in the form of a roll of continuous forms bond paper having a basis weight of about 15 to about 24 lb/1300 $m^2$ (6.8 to 10.9 kg/121 $m^2$) can be converted to a standard perforated continuous form on a continuous forms press at a press speed of about 1300 to about 2000 feet (390 m to 600 m) per minute. The preferred paper according to the invention, in the form of a roll of continuous forms bond paper having a basis weight of about 15 to about 24 lb/1300 $ft^2$ (6.8 to 10.9 kg/121 $m^2$), and that is sized at an addition rate of at least about 2.2 lb/ton (1 kg per 0.9 metric ton) can be converted to a standard perforated continuous form on the Hamilton-Stevens continuous forms press at a press speed of at least about 1775 feet (541 m) per minute, preferably at least about 1900 feet (579 m) per minute.

The paper of this invention can also be made into a roll of envelope paper having a basis weight of about 15 to about 24 lb/1300 $ft^2$ (6.8 to 10.9 kg/121 $m^2$) that is sized at an addition rate of at least about 2.2 lb/ton (1 kg/0.9 metric ton). The paper can be converted into at least about 900 envelopes per minute, preferably at least about 1000 per minute on a Winkler & Dunnebier CH envelope folder.

The paper of this invention can be run at a speed of at least about 58 sheets per minute on a high speed IBM 3825 sheet-fed copier with less than 1 in 10,000 double feeds or jams.

The paper of this invention is capable of running on a high-speed, continuous forms laser printer with a rate of billowing at least about 10% less, preferably about 20% less, than that produced when running on the same printer, a roll of continuous forms bond paper having the same basis weight and sized at the same level with an AKD size made from a mixture of stearic and palmitic acids, after 10 minutes of running time.

The paper of this invention is capable of running on a high-speed IBM 3825 sheet-fed copier at a speed of about 58 sheets per minute with at least about 50% fewer, preferably about 70% fewer, double feeds or jams than the number of double feeds or jams caused when running on the same copier, sheets of paper having the same basis weight and sized at the same level with an AKD size made from a mixture of stearic and palmitic acids.

The paper of this invention is also capable of being converted to a standard perforated continuous form on a continuous forms press at a press speed at least 3% higher, preferably at least 5% higher, than paper having the same basis weight and sized at the same level with an AKD size made from a mixture of stearic and palmitic acids.

The paper of this invention is also capable of being made into a roll of envelope paper having a given basis weight and sized at a given level, that is capable of being converted into at least 3% more envelopes per minute on a Winkler and Dunnebier CH envelope folder than paper having the same basis weight and sized at the same level with an AKD size made from a mixture of stearic and palmitic acids can be converted on the same envelope folder.

In the following examples all percentages and ratios are by mole, unless otherwise indicated.

EXAMPLES

Example 1

Paper for evaluation on the IBM 3800 was prepared on a pilot paper machine.

To make a typical forms bond papermaking stock, the pulp furnish (three parts Southern hardwood kraft pulp and one part Southern softwood kraft pulp) was refined to 425 ml Canadian Standard Freeness (C.S.F.) using a double disk refiner. Prior to the addition of the filler to the pulp furnish (10% medium particle-size precipitated calcium carbonate), the pH (7.8–8.0), alkalinity (150–200 ppm), and hardness (100 ppm) of the papermaking stock were adjusted using the appropriate amounts of $NaHCO_3$, NaOH, and $CaCl_2$.

The 2-oxetanone sizing agents were prepared by methods used conventionally to prepare commercial alkyl ketene dimers, i.e., acid chlorides from a mixture of saturated and unsaturated fatty acids are formed using a conventional chlorination agent (phosphorus trichloride), and the acid chlorides are dehydrochlorinated in the presence of a suitable base (triethyl amine). The unsaturated fatty acid feedstock was Emersol 221, available from Henkel-Emery, Cincinnati, Ohio, and the saturated fatty acid feedstock was Emery 135, also available from Henkel-Emery. Emersol 221 is a mixture of 73% oleic acid, 8% linoleic acid, 6% palmitoleic acid, 3% myritoleic acid, 1% linolenic acid, and 9% saturated fatty acids (by weight %). Emery 135 is a mixture of 50% palmitic acid, 45.5% stearic acid, 2.5% myristic acid, and 2% other fatty acids (by weight %).

The 2-oxetanone sizing agent emulsions were prepared according to the disclosure of U.S. Pat. No. 4,317,756, which is incorporated herein by reference, with particular reference to Example 5 of the patent.

The following addition sequence was used. Quaternary amine-substituted cationic starch (0.75%), was added at the second mixer. The 2-oxetanone sizing agent emulsion was added at the third mixer. The mixtures of 2-oxetanone compounds were primarily liquid at room temperature. Alum (0.2%) was added at the inlet side of the fan pump. Reten® 235 retention aid (0.025%), available from Hercules Incorporated, Wilmington, Del., was added after the fan pump. The stock temperature at the headbox and white water tray was controlled at 110° F. (43.3° C.).

The wet presses were set at 40 psi gauge. A dryer profile that gave 1–2% moisture at the size press and 4–6% moisture at the reel was used (77 f.p.m. (feet per minute)). Approximately 35 lb/ton of an oxidized corn starch and 1 lb/ton of NaCl were added at the size press (130° F. (54.4° C.), pH 8). Calender pressure and reel moisture were adjusted to obtain a Sheffield smoothness of 150 flow units at the reel (Column #2, felt side up).

A 35 minute roll of paper from each papermaking condition was collected (i.e., a roll was made by collecting paper for 35 minutes) and converted on a commercial forms press to two boxes of standard 8½×11" forms. Samples were also collected before and after each 35 minute roll for natural aged size testing, basis weight (46 lb/3000 $ft^2$), and smoothness testing.

The converted paper was allowed to equilibrate in the printer room for at least one day prior to evaluation. Each box of paper provided a 10–14 minute (220 f.p.m.) evaluation on the IBM 3800. All samples were tested in duplicate. A standard acid fine paper was run for at least two minutes between each evaluation to reestablish initial machine conditions. A summary of the test results is given in Table 1. In the Table, E-221 is EMERSOL 221 and E-135 is EMERY 135.

TABLE 1

| Starting Material for Making Sizing Agent | Size Addition Level (lb/ton) | Converting Performance Maximum Billow (inches) | Seconds to 3" |
|---|---|---|---|
| EMERY 135 (control) | 2.2 | 3.25 | 180 |
| EMERY 135 (control) | 3.0 | 3.75 | 180 |
| EMERSOL 221 (control) | 2.2 | 2.125 | >600 |
| EMERSOL 221 (control) | 3.0 | 2.125 | >600 |
| EMERSOL 221 (control) | 4.0 | 3.50 | 420 |
| 4:1 E-221:E-135 | 2.2 | 2.125 | >600 |
| 4:1 E-221:E-135 | 3.0 | 2.25 | >600 |
| 4:1 E-221:E-135 | 4.0 | 2.50 | >600 |
| 7:3 E-221:E-135 | 2.2 | 2.25 | >600 |
| 7:3 E-221:E-135 | 3.0 | 2.25 | >600 |
| 7:3 E-221:E-135 | 4.0 | 2.875 | >600 |
| 1:1 E-221:E-135 | 2.2 | 2.125 | >600 |
| 1:1 E-221:E-135 | 3.0 | 2.25 | >600 |
| 1:1 E-221:E-135 | 4.0 | 3.375 | 410 |

The height of billowing in inches between two defined rolls on the IBM 3800, and the rate at which billowing occurred (inches of increase in billowing per second), were used to measure the effectiveness of each sizing composition. The faster and higher the sheet billows, the worse the converting performance. The 2-oxetanone sizing agents made from a mixture of saturated and unsaturated fatty acids gave much better paper handling performance than the ketene dimer made from saturated fatty acid. The 2-oxetanone sizing agents made from a mixture of saturated and unsaturated fatty acids gave paper handling performance as good, or better, than the ketene dimer made from unsaturated fatty acid, particularly at the highest size addition level.

Example 2

The sizing efficiencies of 2-oxetanone sizing agents made from mixtures of saturated and unsaturated fatty acid feedstocks were measured in a second pilot paper machine evaluation. HST sizing was used to measure sizing efficiency. The Hercules Size Test (HST) is a standard test in the industry for measuring the degree of sizing. This method employs an aqueous dye solution as the penetrant to permit optical detection of the liquid front as it moves through the sheet. The apparatus determines the time required for the reflectance of the sheet surface not in contact with the penetrant to drop to a predetermined percentage of its original reflectance. All HST testing data reported measure the seconds to 80% reflection with 1% formic acid ink mixed with naphthol green B dye unless otherwise noted. The use of formic acid ink is a more severe test than neutral ink and tends to give faster test times. High HST values are better than low values. The amount of sizing desired depends upon the kind of paper being made and the system used to make it.

As shown in Table 2, two 2-oxetanone sizing agents prepared from mixtures of a saturated fatty acid feed (Emery 135, a mixture of palmitic and stearic acids) and an unsaturated fatty acid feed (Emersol 221) were evaluated for sizing efficiency against a 2-oxetanone sizing agent made from the unsaturated fatty acid feed. The mixed fatty acid feeds evaluated were: 20% saturated fatty acid feed, 80% unsaturated fatty acid feed, and 50% saturated fatty acid feed, 50% unsaturated fatty acid feed. The 2-oxetanone sizing agents and their emulsions were made as described in Example 1.

Paper for sizing efficiency testing was made on a small pilot paper machine. To make a typical fine paper-making stock, the pulp furnish (three parts hardwood kraft pulp and one part softwood kraft pulp) was refined to 425 ml Canadian Standard Freeness (C.S.F.) using a double disk refiner. Prior to the addition of the filler to the pulp furnish (20% medium particle-size precipitated calcium carbonate), the pH (7.8–8.0), alkalinity (150–200 p.p.m.), and hardness (100 p.p.m.) of the paper making stock were adjusted using the appropriate amounts of $NaHCO_3$, NaOH, and $CaCl_2$.

The following wet end addition sequence was used: 2-oxetanone sizing agents were combined with cationic starch (0.4%) and was added to the paper machine after the stuff box, followed by separate addition of filler (20%), alum (0.1%), and a high molecular weight anionic polyacrylamide retention aid (0.01%). Stock temperature at the white water tray was controlled at 43° C. A dryer profile that gave 5–6% moisture at the reel was used (3.0 meters/minute paper machine speed). The results of on machine and natural aged sizing testing of the paper made by this method are shown in Table 2.

Clearly, adding saturated fatty acid to the completely unsaturated fatty acid feed stock gave a 2-oxetanone sizing agent with increased sizing efficiency. Based on the results of IBM 3800 testing, this increase in sizing efficiency is obtained at as good or better paper handling performance.

TABLE 2

| Starting Material for Making Sizing Agent | Size Addition Level (lb/ton) | On-Machine HST (sec) | 7-Day HST (sec) |
|---|---|---|---|
| EMERY 135 (control) | 2.0 | 12 | 21 |
| EMERSOL 221 (control) | 2.0 | 1 | 1 |
| 1:1 EMERSOL 221/EMERY 135 | 2.0 | 3 | 4 |
| 4:1 EMERSOL 221/EMERY 135 | 2.0 | 3 | 2 |
| EMERY 135 (control) | 3.0 | 142 | 130 |
| EMERSOL 221 (control) | 3.0 | 7 | 7 |
| 1:1 EMERSOL 221/EMERY 135 | 3.0 | 38 | 44 |
| 4:1 EMERSOL 221/EMERY 135 | 3.0 | 15 | 24 |
| EMERY 135 (control) | 4.0 | 283 | 242 |
| EMERSOL 221 (control) | 4.0 | 32 | 35 |
| 1:1 EMERSOL 221/EMERY 135 | 4.0 | 75 | 103 |
| 4:1 EMERSOL 221/EMERY 135 | 4.0 | 73 | 58 |

From the data in Examples 1 and 2 it can be seen that the invention provides paper with equal or better runability and higher sizing efficiency (more HST sizing at equal levels of addition) than comparable sizing agents made primarily from unsaturated fatty acids. In addition, the data in Example 1 shows that the invention provides better converting performance than comparable sizing agents made primarily from saturated fatty acids. Consequently, the invention provides the best balance of sizing efficiency and converting performance.

Example 3

This Example shows preparation of a 2-oxetanone sizing agent made from a mixture of unsaturated fatty acid and a fatty acid source containing saturated fatty acid varying from 16 weight % to 60 weight %.

2-oxetanone sizing agents were prepared by methods used conventionally to prepare commercial alkyl ketene dimers. That is, acid chlorides were prepared from a mixture of fatty acids using a conventional chlorination agent (phosphorus trichloride), and the acid chlorides were dehydrochlorinated in the presence of a suitable base (triethyl amine). The unsaturated fatty acid feedstock was Pamak®131, available from Hercules Incorporated, and the a fatty acid source containing saturated fatty acids was Pamolyn® Saturates, also available from Hercules Incorporated. Pamolyn Saturates contains on average 25 weight % saturated fatty acids (primarily stearic acid) and 75 weight % unsaturated fatty acid (typically 42 weight % oleic acid and 33 weight % linoleic acid). One 2-oxetanone control sizing agent was made by mixing Pamolyn Saturates with Pamak 131, such that the resulting blend contained 10 weight % saturated fatty acid. Another 2-oxetanone sizing agent was made from Pamolyn Saturates. Two controls 2-oxetanone sizing agents were prepared, one made using Emersol 221 and another made using Pamak 131. 2-oxetanone sizing agent emulsions were prepared according to the disclosure of U.S. Pat. No. 4,317,756, which is incorporated herein by reference, with particular reference to Example 5 of the patent, and the samples were evaluated as internal sizes.

Laboratory tests indicated that the 2-oxetanone sizing agent made from Pamolyn Saturates by itself gave the best sizing performance. The blend of P-131 and Pamolyn Saturates had sizing comparable to the other control samples.

It is not intended that the examples given here should be construed to limit the invention, but rather they are submitted to illustrate some of the specific embodiments of the invention. Various modifications and variations of the present invention can be made without departing from the scope of the appended claims.

We claim:

1. A sizing composition for paper made under alkaline conditions that is not solid at 35° C. and comprises a mixture of 2-oxetanone compounds that are the reaction product of a reaction mixture comprising fatty acids from:

(a) a feedstock comprising primarily unsaturated fatty acid, and (b) a feedstock comprising primarily straight chain saturated fatty acid, provided that about 10–85 mole % of the fatty acids comprise the straight chain saturated fatty acid and about 90–15 mole % of the fatty acids comprise the unsaturated fatty acid.

2. The composition of claim 1 wherein the composition is not solid at 25° C.

3. The composition of claim 1 wherein the composition is not solid at 20° C.

4. The composition of claim 1 wherein the composition is liquid at 35° C.

5. The composition of claim 1 wherein the composition is liquid at 25° C.

6. The process of claim 5 wherein the 2-oxetanone compounds are 2-oxetanone dimers.

7. The composition of claim 5 wherein the fatty acid comprises about 20–60 mole % of the straight chain of the saturated fatty acid and about 80–40 mole % unsaturated fatty acid.

8. The composition of claim 7 wherein the fatty acids are monocarboxylic acids or monocarboxylic acid chlorides having 16–18 carbon atoms.

9. The composition of claim 8 wherein the mole ratio of the unsaturated fatty acid feedstock to the straight chain saturated fatty acid feedstock is about 4:1.

10. The composition of claim 8 wherein the mole ratio of the unsaturated fatty acid feedstock to the straight chain saturated fatty acid feedstock is about 7:3.

11. The composition of claim 7 wherein the fatty acids are monocarboxylic acid or monocarboxylic acid halides having 6–26 carbon atoms, the straight chain saturated fatty acid feedstock comprises at least 80 mole % of the straight chain saturated fatty acid, the unsaturated fatty acid feedstock comprises at least 70 mole % of the unsaturated fatty acid, and the mole ratio of the unsaturated fatty acid feedstock to the straight chain saturated acid feedstock is about 1:1 to 4:1.

12. The process of claim 11 wherein the 2-oxetanone compounds are 2-oxetanone dimers.

13. The composition of claim 11 wherein the reaction mixture additionally comprises (c) an alkyl dicarboxylic acid having 6–36 carbon atoms.

14. An aqueous emulsion comprising water and 10–30 weight % of the sizing composition of claim 11.

15. The composition of claim 5 wherein the fatty acid comprises about 30–55 mole % of the straight chain of the saturated fatty acid and about 70–45 mole % unsaturated fatty acid.

16. The composition of claim 5 wherein the fatty acids are monocarboxylic acids or monocarboxylic acid halides having 12–22 carbon atoms.

17. The composition of claim 5 wherein the reaction mixture additionally comprises (c) an alkyl dicarboxylic acid having 6–44 carbon atoms.

18. The composition of claim 17 wherein the dicarboxylic acid has 8–36 carbon atoms.

19. The composition of claim 17 wherein the dicarboxylic acid has 9–10 carbon atoms.

20. An aqueous emulsion comprising water and 1–60 weight % of the sizing composition of claim 17.

21. An aqueous emulsion comprising water and 6–50 weight % of the sizing composition of claim 5.

22. The aqueous emulsion of claim 21 wherein the 2-oxetanone compounds are 2-oxetanone dimers.

23. The composition of claim 1 wherein the composition is liquid at 20° C.

24. The composition of claim 1 wherein the fatty acids are monocarboxylic acids or monocarboxylic acid halides having 6–26 carbon atoms.

25. The composition of claim 1 wherein the straight chain saturated fatty acid is selected from the group consisting of stearic, myristic, palmitic, margaric, pentadecanoic, decanoic (capric), undecanoic, dodecanoic (lauric), tridecanoic, nonadecanoic, arachidic, and behenic acids and acid chlorides, and mixtures thereof, and the unsaturated fatty acid is selected from the group consisting of oleic, linoleic, dodecenoic, tetradecenoic (myristoleic), hexadecenoic (palmitoleic), octadecadienoic (linolelaidic), octadecatrienoic (linolenic), eicosenoic (gadoleic), eicosatetraenoic (arachidonic), docosenoic (erucic), docosenoic (brassidic), and docosapentaenoic (clupanodonic) acids and acid chlorides, and mixtures thereof.

26. The composition of claim 1 wherein the straight chain saturated fatty acid feedstock comprises at least 80 mole % of the straight chain saturated fatty acid and the unsaturated fatty acid feedstock comprises at least 70 mole % of the unsaturated fatty acid.

27. The composition of claim 1 wherein the straight chain saturated fatty acid feedstock comprises at least about 95 mole % of the straight chain saturated fatty acid and the unsaturated fatty acid feedstock comprises at least about 90 mole % of the unsaturated fatty acid.

28. The composition of claim 1 wherein the mole ratio of the unsaturated fatty acid feedstock to the straight chain saturated fatty acid feedstock is about 1:1–4:1.

29. The composition of claim 1 wherein the mole ratio of the unsaturated fatty acid feedstock to the straight chain saturated fatty acid feedstock is about 1:1.

30. An aqueous emulsion comprising water and 6–50 weight % of the sizing composition of claim 1.

31. A sizing composition that is not a solid at 35° C. and comprises a mixture of 2-oxetanone compounds that are the reaction product of a mixture of fatty acids comprising about 10–85 mole % straight chain saturated fatty acid and 90–15 mole % unsaturated fatty acid.

32. The composition of claim 31 that is not solid at 25° C.

33. The composition of claim 31 that is a liquid at 25° C.

34. The composition of claim 33 wherein the mixture of fatty acids comprises about 20–60 mole % of the straight saturated fatty acid and about 80–40 mole % of the unsaturated fatty acid.

35. The composition of claim 34 wherein the fatty acids are monocarboxylic acids or monocarboxylic acid halides having 6–44 carbon atoms.

36. The composition of claim 33 wherein the mixture of fatty acids comprises about 30–55 mole % straight saturated fatty acid and about 70–45 mole % of the unsaturated fatty acid.

37. The composition of claim 36 wherein the fatty acids are monocarboxylic acids or monocarboxylic acid halides having 12–22 carbon atoms.

38. The composition of claim 33 wherein the fatty acids are monocarboxylic acids or monocarboxylic acid halides having 6–26 carbon atoms.

39. The composition of claim 33 wherein the fatty acids are monocarboxylic acid or monocarboxylic acid halide having 12–22 carbon atoms.

40. The composition of claim 33 wherein the reaction mixture further comprises at least one alkyl dicarboxylic acid having 6–44 carbon atoms.

41. The composition of claim 40 wherein the alkyl dicarboxylic acid has 8–36 carbon atoms.

42. An aqueous emulsion comprising water and 1–60 weight % of the sizing composition of claim 31.

43. A process of preparing a 2-oxetanone sizing agent from fatty acids comprising:

(1) providing
  (a) at least one feedstock comprising primarily unsaturated fatty acid, and
  (b) at least one feedstock comprising primarily straight chain saturated fatty acid, and (2) reacting the the fatty acids to form a 2-oxetanone sizing composition that is not a solid at 35° C., provided that about 10–85 mole % of the fatty acids comprise the straight chain saturated fatty acid and about 90–15 mole % of the fatty acids comprise the unsaturated fatty acid.

44. The process of claim 43 wherein:

(a) the 2-oxetanone sizing agent is a liquid at 25° C., (b) the fatty acids comprise about 20–75 mole % straight chain saturated fatty acid and 80–25 mole % unsaturated fatty acid, (c) the straight chain saturated fatty acid feedstock comprises at least 95% of the straight chain saturated fatty acid, and (d) the unsaturated fatty acid feedstock comprises at least 90% of the unsaturated fatty acid.

45. The process of claim 44 wherein the fatty acids comprise 30–55 mole % of the straight chain saturated fatty acid and 70–45 mole % of the unsaturated fatty acid, and the fatty acids are monocarboxylic acid or nonocarboxylic acid halide having 10–26 carbon atoms.

46. The process of claim 44 further comprising providing (c) at least one alkyl dicarboxylic acid having 8–44 carbon atoms and reacting at least one acid alkyl dicarboxylic with the fatty acids.

47. The process of claim 43 wherein the 2-oxetanone compounds are 2-oxetanone dimers.

48. A process for preparing a 2-oxetanone sizing agent comprising;

(a) providing unsaturated and straight chain saturated fatty acids, the fatty acids comprising
  (1) about 10–85 mole % of the straight chain saturated fatty acid, and
  (2) about 90–15 mole % of the unsaturated fatty acid, and (b) reacting them to form a 2-oxetanone sizing agent that is not a solid at 35° C.

49. The process of claim 48 wherein:

(a) the 2-oxetanone sizing agent is a liquid at 25° C., and (b) the fatty acid comprises about 30–55 mole % of the saturated fatty acid and 70–45 mole % of the unsaturated fatty acid.

* * * * *